United States Patent
Han

(10) Patent No.: US 10,161,921 B2
(45) Date of Patent: Dec. 25, 2018

(54) FUNCTIONAL LABEL, HAVING LACTOBACILLUS SEPARATOR MEMBRANE AND USING SELECTIVE DISSOLUTION FOR DETECTING EXTERNAL TEMPERATURE, FOR CHECKING FRESHNESS OF STORAGE MATERIAL

(71) Applicant: Youn Suk Han, Gunpo-si (KR)

(72) Inventor: Youn Suk Han, Gunpo-si (KR)

( * ) Notice: Subject to any disclaimer, the term of this patent is extended or adjusted under 35 U.S.C. 154(b) by 161 days.

(21) Appl. No.: 15/317,488

(22) PCT Filed: Jun. 8, 2015

(86) PCT No.: PCT/KR2015/005705
§ 371 (c)(1),
(2) Date: Dec. 9, 2016

(87) PCT Pub. No.: WO2015/190775
PCT Pub. Date: Dec. 17, 2015

(65) Prior Publication Data
US 2017/0131249 A1    May 11, 2017

(30) Foreign Application Priority Data
Jun. 9, 2014   (KR) .......................... 10-2014-0069195

(51) Int. Cl.
*G01N 31/22* (2006.01)
*G01K 11/06* (2006.01)
(Continued)

(52) U.S. Cl.
CPC .............. *G01N 31/229* (2013.01); *C12Q 1/04* (2013.01); *G01K 11/06* (2013.01); *G01K 11/12* (2013.01); *G01N 31/221* (2013.01); *G01N 33/02* (2013.01)

(58) Field of Classification Search
None
See application file for complete search history.

(56) References Cited

U.S. PATENT DOCUMENTS

2014/0127738 A1* 5/2014 Lee .......................... C12Q 1/02
435/29

FOREIGN PATENT DOCUMENTS

KR    1020020066157    8/2002
KR    1020020086597    11/2002
(Continued)

OTHER PUBLICATIONS

International Search Report—PCT/KR2015/005705 dated Jul. 13, 2015.

*Primary Examiner* — Thomas J. Visone
(74) *Attorney, Agent, or Firm* — Cantor Colburn LLP

(57) ABSTRACT

Provided is an exterior temperature-detectable selectively dissoluble lactic acid bacteria separation membrane functional label for checking freshness of a stored substance. More particularly, provided is an exterior temperature-detectable selectively dissoluble lactic acid bacteria separation membrane functional label for checking freshness of a stored substance which includes a lactic acid bacteria layer and a pH indicator layer that are attached to an upper part of a label such that they are separated from each other via a separation membrane to check decay of a stored substance when a separation membrane for detecting a temperature change is dissolved at an exterior temperature of −10 to 40° C.

9 Claims, 3 Drawing Sheets

(51) Int. Cl.
*G01N 33/02* (2006.01)
*C12Q 1/04* (2006.01)
*G01K 11/12* (2006.01)

(56) References Cited

FOREIGN PATENT DOCUMENTS

| | | | |
|---|---|---|---|
| KR | 101012125 | 2/2011 | |
| KR | 1020110086950 | 8/2011 | |
| WO | WO-2005054800 A1 * | 6/2005 | ............. G01K 11/06 |

* cited by examiner

FUNCTIONAL LABEL, HAVING LACTOBACILLUS SEPARATOR MEMBRANE AND USING SELECTIVE DISSOLUTION FOR DETECTING EXTERNAL TEMPERATURE, FOR CHECKING FRESHNESS OF STORAGE MATERIAL

TECHNICAL FIELD

The present invention relates to an exterior temperature-detectable selectively dissoluble lactic acid bacteria separation membrane functional label for checking freshness of a stored substance. More particularly, the present invention relates to an exterior temperature-detectable selectively dissoluble lactic acid bacteria separation membrane functional label for checking freshness of a stored substance which includes a lactic acid bacteria layer and a pH indicator layer that are attached to an upper part of a label such that they are separated from each other via a separation membrane to check decay of a stored substance when a separation membrane for detecting a temperature change is dissolved at an exterior temperature of −10 to 40° C.

BACKGROUND ART

Substances, such as foods, that easily spoil are stored or transported in a refrigerated state. In this case, when storage temperature is changed or food is exposed to the outside, the food may go bad. If it is possible to determine whether or not the food is kept refrigerated well until the food exposed to the outside is finally used, food poisoning or the like resulting from growth of putrefying bacteria can be prevented and safety of food can be effectively managed.

It is possible to chemically or physically measure and display a change history in exterior air over time during food storage. Although it is possible to physically measure time and degree through change in temperature of the exterior environment, but it is more difficult to individually measure how much the temperature of liquid food changes through the substance in a storage container due to various factors such as conditions of a storage area and heat transfer capacity of the storage container.

It is more difficult to determine storage temperature, exposure time and the like in order to determine if stored food spoils or not. It is more difficult to biologically determine if putrefying bacteria grow or not based on various types of temperature changes than to physically measure temperature changes. It is possible to predict the time and temperature required for growth of putrefying bacteria, but it is impossible to physically and chemically predict whether putrefying bacteria actually grow or not via continuously changed temperatures and different exposure times in food storage areas.

A label that can be attached to the outside of a food storage container containing lyophilized organic acid, a medium powder, a pH indicator and distilled water is produced and is used to determine whether or not a stored substance spoils depending on cumulative temperature changes.

Korean Patent Laid-open No. 2002-86597 discloses a system for displaying time and temperature suitable for activation and Korean Patent No. 1012125 discloses a label for determining growth of food putrefying bacteria depending on cumulative storage temperature changes.

DISCLOSURE

Technical Problem

Therefore, the present invention has been made in view of the above problems, and it is an object of the present invention to provide an exterior temperature-detectable selectively dissoluble lactic acid bacteria separation membrane functional label for checking freshness of a stored substance depending on cumulative storage temperature changes.

Technical Solution

In accordance with the present invention, the above and other objects can be accomplished by the provision of an exterior temperature-detectable selectively dissoluble lactic acid bacteria separation membrane functional label for checking freshness of a stored substance which includes a lactic acid bacteria layer and a pH indicator layer that are attached to an upper part of a label such that they are separated from each other via a separation membrane to check decay of a stored substance when a separation membrane for detecting a temperature change is dissolved at an exterior temperature of −10 to 40° C.

Advantageous Effects

The exterior temperature-detectable selectively dissoluble lactic acid bacteria separation membrane functional label according to the present invention includes a separation membrane which can be attached to the outside of a food storage container wherein the separation membrane is dissolved and changes color when it undergoes the same temperature change as a stored substance. Based on this color change, it is possible to determine freshness of the stored substance.

DESCRIPTION OF DRAWINGS

The above and other objects, features and other advantages of the present invention will be more clearly understood from the following detailed description taken in conjunction with the accompanying drawings, in which.

BEST MODE

Figure 1:
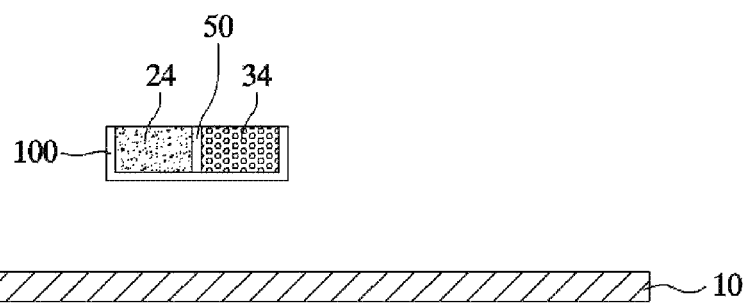
FIGS. 1 to 8 are exploded sectional views illustrating a functional label for checking freshness of a stored substance according to the present invention.
Figure 2:
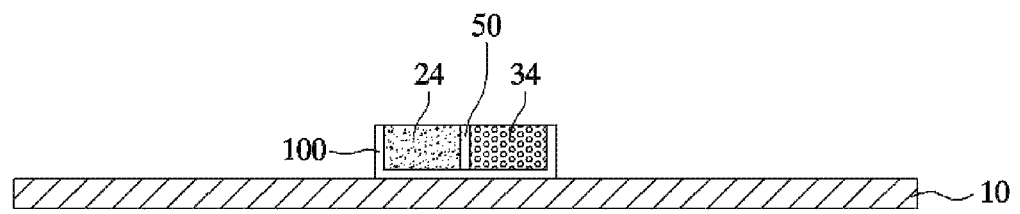
Figure 3:
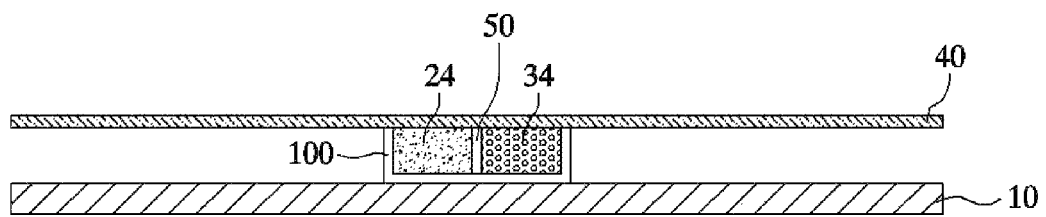

The present invention relates to an exterior temperature-detectable selectively dissoluble lactic acid bacteria separation membrane functional label for checking freshness of a stored substance including: a pH indicator layer 24 attached to the surface of an upper part of a label 10; a lactic acid bacteria layer 34 attached to the surface of the upper part of the label 10 and separated from the pH indicator layer 24; and a separation membrane 50 for separating the pH indicator layer 24 from the lactic acid bacteria layer 34, wherein the pH indicator layer 24 includes any one indicator selected from a pH indicator powder 20 and a pH indicator liquid 22, the lactic acid bacteria layer 34 includes a lactic acid bacteria liquid 32, and the separation membrane 50 includes a separation membrane for detecting an exterior temperature selectively dissolved at an exterior temperature of −10 to 40 degrees.

In the present invention, the separation membrane 50 includes sugar, starch, a phase-transfer coating agent and a phase-transfer inducing catalyst and the phase-transfer coating agent is a linseed oil free of odor and cyanide (—CN) toxicity which is prepared by heating linseed at 100° C. for 20 minutes, removing moisture from the linseed, rapidly cooling the residue, obtaining an linseed oil from the rapidly cooled linseed in an oil extruder at a temperature of 100° C., filtering the linseed oil through a 200 mesh sieve to obtain the filtered linseed oil, allowing the filtered linseed oil to be precipitated for 20 days and collecting the supernatant to obtain a purified linseed oil.

The present invention relates to an exterior temperature-detectable selectively dissoluble lactic acid bacteria separation membrane functional label for checking freshness of a stored substance including: a pH indicator layer 24 attached to the surface of an upper part of a label 10; a lactic acid bacteria layer 34 attached to the surface of the upper part of the label 10 and separated from the pH indicator layer 24; and a separation membrane 50 for separating the pH indicator layer 24 from the lactic acid bacteria layer 34, wherein the pH indicator layer 24 includes a pH indicator liquid 22, the lactic acid bacteria layer 34 includes a lactic acid bacteria powder 30 and the separation membrane 50 includes a separation membrane for detecting an exterior temperature which is selectively dissolved at an exterior temperature of −10 to 40 degrees.

The label of the present invention includes the pH indicator layer 24 and the lactic acid bacteria layer 34 which are separated from each other in a container 100.

The label of the present invention includes a plurality of containers 100 attached to the surface of the upper part of the label 10 and the separation membranes of respective containers 100 are selectively dissolved at different temperatures.

The label of the present invention includes a surface separation membrane 40 further coated on the separation membrane 50.

The present invention relates to a temperature-detecting label that can check whether a stored substance, i.e., frozen food such as frozen dumplings, is kept fresh when an exterior temperature increases from −10 to 40° C.

Figure 4:
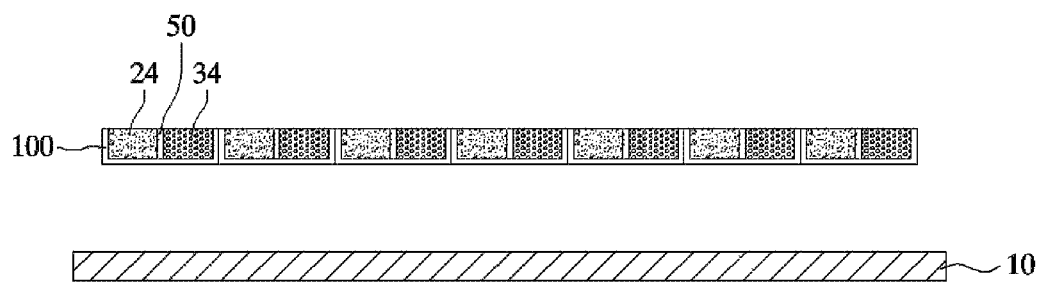
Figure 5:
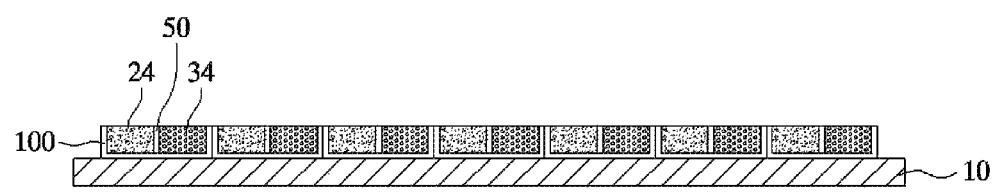
Figure 6:
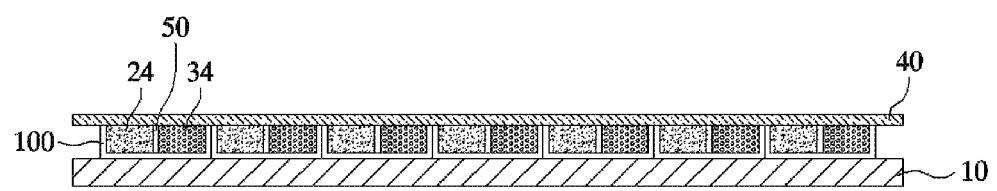
Figure 7:
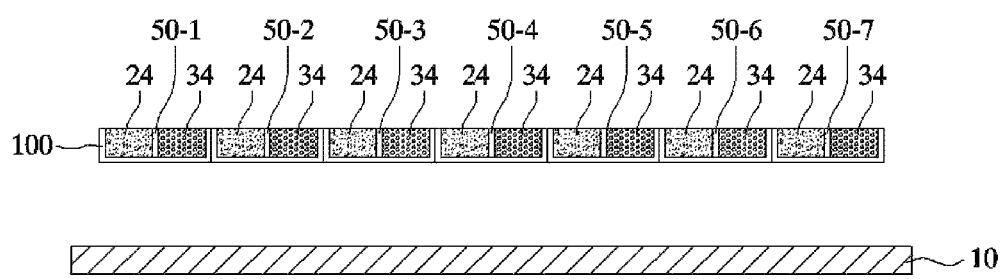
Figure 8:
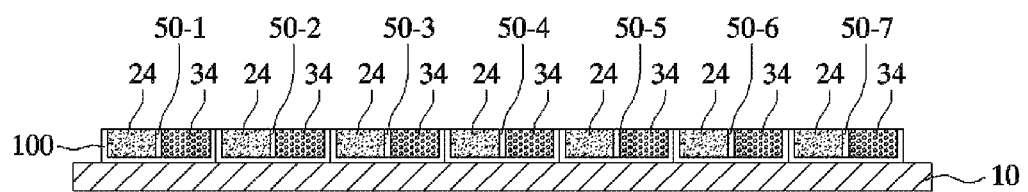

As shown in FIGS. 4 to 6, the label of the present invention preferably includes a pH indicator layer 24 and a lactic acid bacteria layer 34 which are separated from each other in a container 100.

As shown in FIGS. 4 to 6, the label of the present invention includes a plurality of containers 100 attached to the surface of the upper part of the label 10 and separation membranes (50-1, 50-2, 50-3, 50-4, 50-5, 50-6, 50-7, 50-8 and 50-9) of the respective containers 100 are selectively dissolved at different temperatures. For this reason, when the respective separation membranes are selectively dissolved at different temperatures, the pH indicator layer 24 and the lactic acid bacteria layer 34 separated from each other via each separation membrane are mixed, thus exhibiting different colors of indicators depending on reactions.

Prior to attachment, the lactic acid bacteria layer and the pH indicator in the label 10 of the present invention are separated from each other via the separation membrane 50 selectively dissolved at an exterior temperature of −10 to 40° C.

The label 10 of the present invention includes the separation membrane 50 which is selectively dissolved at the exterior temperature of −10 to 40° C. when an adhesion part such as a double-sided tape is peeled off and the label 10 is attached and the exterior temperature is increased from −10 to 40° C., which is attached to the label 10.

The present invention provides a method of determining decay feasibility of a stored substance including: attaching a label to an exterior container of a stored substance; dissolving a separation membrane 50 when an exterior temperature increases from −10 to 40° C. and mixing lactic acid bacteria with a pH indicator when the coating layer 50 is dissolved; and observing the color of the label after the mixing between the lactic acid bacteria and the pH indicator and determining that decay has occurred when the color indicates an acidic condition.

The determination of whether a stored substance has decayed can be carried out by exposing the label of the present invention to various temperatures and then comparing the color of the pH indicator when the separation membrane 50 is dissolved. The method according to the present invention is useful for determining decay feasibility of a stored substance depending on cumulative storage temperature changes. Regarding the label of the present invention, the lactic acid bacteria are mixed with the pH indicator in the label attached to the outer container of the stored substance, when the temperature of the stored substance increases or changes due to accumulation of exterior temperature changes during storage. According to the present invention, when acidic pH is obtained by an organic acid, decay feasibility can be determined by checking whether or not a pH marker (indicator) indicates an acidic color.

According to the present invention, the separation membrane 50 can be temperature-selectively dissolved at a temperature of −10 to 40° C. and is a soft resin separation membrane for detecting a temperature change that is selectively dissolved at an exterior temperature of −10 to 40° C.

The separation membrane 50 according to the present invention includes both a natural soft resin separation membrane and a synthetic soft resin separation membrane. The synthetic soft resin separation membrane according to the present invention is preferably a separation membrane made of sugar.

In the present invention, a material for producing the separation membrane 50 is preferably a food additive sugar composition. In the present invention, the separation membrane 50 is preferably selected from maltose, glucose, fructose and sucrose.

Among the food additive sugar composition used for the separation membrane according to the present invention, monosaccharide is classified into biose, triose, tetraose, pentose and hexose depending on the number of carbon atoms and the most important monosaccharide is hexose.

Glucose is an essential substance for glycometabolism, which is the most basic energy source of biological systems and is rich in vegetables and fruits, in particular, grape juices.

Fructose is present in fruits and honey, is the sweetest sugar and is a constituent unit of sucrose and invert sugar. Galactose is combined with glucose and is thus present in the form of a disaccharide, so-called "lactose", and is less sweet than glucose and is not readily soluble in water.

Disaccharides include sucrose, maltose, lactose and the like. Sucrose is a sugar in which glucose is linked to fructose, which is rich in sugar cane and sugar beets. Lactose is rich in animal milk, is relatively less sweet, is not readily soluble in water and is slowly digestible.

Oligosaccharide is a polysaccharide. It is mainly linked as a constituent of glycoprotein or glycolipid to the biomembrane in the cell and is bound to secretory proteins such as the endoplasmic reticulum and the Golgi body, and includes galactooligosaccharides, isomaltooligosaccharides and fructooligosaccharides. Polysaccharides called "complex carbohydrates" are classified into starch, glycogen, and dietary fiber.

Hexosan is starch, and glycogen is carbohydrate stored in animals and is stored in muscle tissue and the liver. Cellulose is a polysaccharide.

The material for the separation membrane 50 used in the present invention is preferably a linseed oil free of odor and cyanide (—CN) toxicity which is prepared by heating linseed at 80 to 120° C. for 10 to 40 minutes, removing moisture from the linseed, rapidly cooling the residue, obtaining an linseed oil from the rapidly cooled linseed in an oil extruder at a temperature of 80 to 120° C., filtering the linseed oil on 200 mesh to obtain the filtered linseed oil, allowing the filtered linseed oil to be precipitated for 10 to 20 days and collecting the supernatant to obtain a purified linseed oil.

The material for the separation membrane 50 used in the present invention preferably includes 5 to 10% by weight of any one antioxidant selected from a green tea extract, γ-tocopherol and rosemary.

The material for the separation membrane 50 used in the present invention further includes 1 to 5% by weight of a phase-transfer inducing catalyst and the phase-transfer inducing catalyst preferably includes: any one selected from rapeseed oil and canola oil; at least one edible phase-transfer inducing catalyst selected from the group consisting of soy protein lecithin, egg lecithin, Tween, monogreen, polyglycerin and ester fatty acid; and at least one monoglyceride selected from the group consisting of glyceryl monooleate, glyceryl monolinoleate, glyceryl monoarachidonate and glyceryl monostearate.

The separation membrane 50 used in the present invention is preferably a mixture of saccharide (sugar), starch, a phase-transfer coating agent and a phase-transfer inducing catalyst which conducts phase-transfer while rotating at a high rate of 3,000 rpm.

The separation membrane according to the present invention that can be temperature-selectively dissolved at −10 to 40° C. depending on exterior temperature changes can be produced by mixing suitable amounts of sugar, starch, a phase-transfer coating agent and a phase-transfer inducing catalyst, controlling ingredients and contents of the mixture, and adjusting the thickness of the separation membrane.

<Example 1> Preparation of Phase-Transfer Water-Soluble Linseed Oil as Phase-Transfer Coating Agent A linseed oil free of odor and cyanide (—CN) toxicity was prepared by heating linseed at 100° C. for 20 minutes, removing moisture from the linseed, rapidly cooling the residue, obtaining an linseed oil from the rapidly cooled linseed in an oil extruder at a temperature of 100° C., filtering the linseed oil through a 200 mesh sieve to obtain the filtered linseed oil, allowing the filtered linseed oil to be precipitated for 20 days and collecting the supernatant to obtain a purified linseed oil.

<Example 2> Preparation of Phase-Transfer Water-Soluble Linseed Oil as Phase-Transfer Coating Agent 50 g of the linseed oil produced in Example 1 and 20 g of tocopherol were mixed with 25 g of water, 5 g of a rapeseed oil was added thereto and was coated while rotating at a high rate of 3,000 rpm to produce a phase-transfer water-soluble linseed oil composition as a phase-transfer coating agent.

<Example 3> Preparation of Phase-Transfer Water-Soluble Linseed Oil as Phase-Transfer Coating Agent 50 g of the linseed oil produced in Example 1 and 20 g of tocopherol were mixed with 25 g of water, 5 g of a canola oil was added thereto and was coated while rotating at a high rate of 3,000 rpm to produce a phase-transfer water-soluble linseed oil composition as a phase-transfer coating agent.

<Example 4> Preparation of Phase-Transfer Water-Soluble Linseed Oil as Phase-Transfer Coating Agent 50 g of the linseed oil produced in Example 1 and 20 g of tocopherol were mixed with 25 g of water, 5 g of glyceryl monooleate was added thereto and was coated while rotating at a high rate of 3,000 rpm to produce a phase-transfer water-soluble linseed oil composition as a phase-transfer coating agent.

<Example 5> Preparation of Phase-Transfer Water-Soluble Linseed Oil as Phase-Transfer Coating Agent 50 g of the linseed oil produced in Example 1 and 20 g of tocopherol were mixed with 25 g of water, 5 g of a phase-transfer inducing catalyst (Tween 60) was added thereto and was coated while rotating at a high rate of 3,000 rpm to produce a phase-transfer water-soluble linseed oil composition as a phase-transfer coating agent.

<Example 6> Production of Separation Membrane Selectively Dissoluble Depending on Exterior Temperature Change A separation membrane including 50% by weight of maltose, 45% by weight of a phase-transfer coating agent and 5% by weight of a phase-transfer inducing catalyst was selectively dissolved at −10° C., a separation membrane including 50% by weight of maltose, 5% by weight of starch, 40% by weight of a phase-transfer coating agent and 5% by weight of a phase-transfer inducing catalyst was selectively dissolved at 0° C., a separation membrane including 50% by weight of maltose, 10% by weight of starch, 35% by weight of a phase-transfer coating agent and 5% by weight of a phase-transfer inducing catalyst was selectively dissolved at 5° C., a separation membrane including 50% by weight of maltose, 20% by weight of starch, 25% by weight of a phase-transfer coating agent and 5% by weight of a phase-transfer inducing catalyst was selectively dissolved at 10° C., a separation membrane including 40% by weight of maltose, 20% by weight of starch, 35% by weight of a phase-transfer coating agent and 5% by weight of a phase-transfer inducing catalyst was selectively dissolved at 15° C., a separation membrane including 50% by weight of maltose, 20% by weight of starch, 25% by weight of a phase-transfer coating agent and 5% by weight of a phase-transfer inducing catalyst was selectively dissolved at 20° C., a separation membrane including 50% by weight of maltose, 25% by weight of starch, 20% by weight of a phase-transfer coating agent and 5% by weight of a phase-transfer inducing catalyst was selectively dissolved at 25° C., a separation membrane including 50% by weight of maltose, 30% by weight of starch, 25% by weight of a phase-transfer coating agent and 5% by weight of a phase-transfer inducing catalyst was selectively dissolved at 30° C., a separation membrane including 40% by weight of maltose, 40% by weight of starch, 15% by weight of a phase-transfer coating agent and 5% by weight of a phase-transfer inducing catalyst was selectively dissolved at 35° C., and a separation membrane including 30% by weight of maltose, 50% by weight of starch, 15% by weight of a phase-transfer coating agent and 5% by weight of a phase-transfer inducing catalyst was selectively dissolved at 40° C.

<Example 7> Production of Separation Membrane Selectively Dissoluble Depending on Exterior Temperature Change A separation membrane including 50% by weight of glucose, 45% by weight of a phase-transfer coating agent and 5% by weight of a phase-transfer inducing catalyst was selectively dissolved at −10° C., a separation membrane including 50% by weight of glucose, 5% by weight of starch, 40% by weight of a phase-transfer coating agent and 5% by weight of a phase-transfer inducing catalyst was selectively dissolved at 0° C., a separation membrane including 50% by weight of glucose, 10% by weight of starch, 35% by weight of a phase-transfer coating agent and 5% by weight of a phase-transfer inducing catalyst was selectively dissolved at 5° C., a separation membrane including 50% by weight of glucose, 20% by weight of starch, 25% by weight of a phase-transfer coating agent and 5% by weight of a phase-transfer inducing catalyst was selectively dissolved at 10° C., a separation membrane including 40% by weight of glucose, 20% by weight of starch, 35% by weight of a phase-transfer coating agent and 5% by weight of a phase-transfer inducing catalyst was selectively dissolved at 15° C., a separation membrane including 50% by weight of glucose, 20% by weight of starch, 25% by weight of a phase-transfer coating agent and 5% by weight of a phase-transfer inducing catalyst was selectively dissolved at 20° C., a separation membrane including 50% by weight of glucose, 25% by weight of starch, 20% by weight of a phase-transfer coating agent and 5% by weight of a phase-transfer inducing catalyst was selectively dissolved at 25° C., a separation membrane including 50% by weight of glucose, 30% by weight of starch, 25% by weight of a phase-transfer coating agent and 5% by weight of a phase-transfer inducing catalyst was selectively dissolved at 30° C., a separation membrane including 40% by weight of glucose, 40% by weight of starch, 15% by weight of a phase-transfer coating agent and 5% by weight of a phase-transfer inducing catalyst was selectively dissolved at 35° C., and a separation membrane including 30% by weight of glucose, 50% by weight of starch, 15% by weight of a phase-transfer coating agent and 5% by weight of a phase-transfer inducing catalyst was selectively dissolved at 40° C.

<Example 8> Production of Separation Membrane Selectively Dissoluble Depending on Exterior Temperature Change A separation membrane including 50% by weight of maltose, 45% by weight of a phase-transfer coating agent and 5% by weight of a phase-transfer inducing catalyst was selectively dissolved at −10° C., a separation membrane including 50% by weight of maltose, 5% by weight of starch, 40% by weight of a phase-transfer coating agent and 5% by weight of a phase-transfer inducing catalyst was selectively dissolved at 0° C., a separation membrane including 50% by weight of maltose, 10% by weight of starch, 35% by weight of a phase-transfer coating agent and 5% by weight of a phase-transfer inducing catalyst was selectively dissolved at 5° C., a separation membrane including 50% by weight of maltose, 20% by weight of starch, 25% by weight of a phase-transfer coating agent and 5% by weight of a phase-transfer inducing catalyst was selectively dissolved at 10° C., a separation membrane including 40% by weight of maltose, 20% by weight of starch, 35% by weight of a phase-transfer coating agent and 5% by weight of a phase-transfer inducing catalyst was selectively dissolved at 15° C., a separation membrane including 50% by weight of maltose, 20% by weight of starch, 25% by weight of a phase-transfer coating agent and 5% by weight of a phase-transfer inducing catalyst was selectively dissolved at 20° C., a separation membrane including 50% by weight of maltose, 25% by weight of starch, 20% by weight of a phase-transfer coating agent and 5% by weight of a phase-transfer inducing catalyst was selectively dissolved at 25° C., a separation membrane including 50% by weight of maltose, 30% by weight of starch, 25% by weight of a phase-transfer coating agent and 5% by weight of a phase-transfer inducing catalyst was selectively dissolved at 30° C., a separation membrane including 40% by weight of maltose, 40% by weight of starch, 15% by weight of a phase-transfer coating agent and 5% by weight of a phase-transfer inducing catalyst was selectively dissolved at 35° C., and a separation membrane including 30% by weight of maltose, 50% by weight of starch, 15% by weight of a phase-transfer coating agent and 5% by weight of a phase-transfer inducing catalyst was selectively dissolved at 40° C.

<Example 9> Selective Dissolution Change of Separation Membrane Depending on Exterior Temperature Change The separation membrane including 50% by weight of maltose, 45% by weight of a phase-transfer coating agent and 5% by weight of a phase-transfer inducing catalyst produced in Example 8 was not dissolved at −10° C. for 0 to 48 hours. In addition, the separation membrane including 50% by weight of maltose, 5% by weight of starch, 40% by weight of a phase-transfer coating agent and 5% by weight of a phase-transfer inducing catalyst produced in Example 8 was not dissolved at 0° C. for 0 to 48 hours.

The separation membrane including 50% by weight of maltose, 10% by weight of starch, 35% by weight of a phase-transfer coating agent and 5% by weight of a phase-transfer inducing catalyst produced in Example 8 was not dissolved at 5° C. for 0 to 48 hours. In addition, the separation membrane including 50% by weight of maltose, 20% by weight of starch, 25% by weight of a phase-transfer coating agent and 5% by weight of a phase-transfer inducing catalyst produced in Example 8 was not dissolved at 10° C. for 0 to 48 hours.

The separation membrane including 40% by weight of glucose, 20% by weight of starch, 35% by weight of a phase-transfer coating agent and 5% by weight of a phase-transfer inducing catalyst produced in Example 8 was not dissolved at 15° C. for 0 to 48 hours. In addition, the separation membrane including 50% by weight of maltose, 20% by weight of starch, 25% by weight of a phase-transfer coating agent and 5% by weight of a phase-transfer inducing catalyst produced in Example 8 was not dissolved at 20° C.

for 0 to 48 hours. In addition, the separation membrane including 50% by weight of maltose, 30% by weight of starch, 25% by weight of a phase-transfer coating agent and 5% by weight of a phase-transfer inducing catalyst produced in Example 8 was not dissolved at 30° C. for 0 to 48 hours.

The lactic acid bacteria powder 30 according to the present invention is preferably a pure lactic acid bacteria powder or a mixture of a lactic acid bacteria powder and a medium powder. The lactic acid bacteria powder 30 according to the present invention is preferably freeze-dried and the medium powder is preferably also freeze-dried.

The lactic acid bacteria liquid 32 according to the present invention is preferably a pure lactic acid bacteria liquid containing distilled water, or a mixture of a lactic acid bacteria liquid containing distilled water and a medium powder or a medium liquid.

The lactic acid bacteria powder 30 or the lactic acid bacteria liquid 32 according to the present invention is preferably mixed with a medium. The lactic acid bacteria according to the present invention is preferably a microorganism that has a similar growth pattern to putrefying food poisoning bacteria, produces an organic acid during growth, thus decreasing pH, and is harmless to humans and the environments. The putrefying food poisoning bacteria according to the present invention is preferably *E. coli* O-157 or *salmonella*.

The lactic acid bacteria for checking decay of a stored substance according to the present invention is preferably selected from the group consisting of yeasts and molds as well as lactic acid bacteria, and is preferably *lactobacillus acidophilus*.

The medium used in the present invention preferably has a composition, pH of which is decreased by an organic acid that is produced as lactic acid bacteria grow and is preferably any one selected from MRS, a medium diluted with MRS (25%), a minimal medium and a minimal medium containing 100 g/L of glucose and is more preferably a medium diluted with MRS (25%).

The lactic acid bacteria powder used in the present invention is preferably a powder mixture of a lactic acid bacteria powder and a medium powder, is preferably a mixture of a lyophilized lactic acid bacteria and a medium powder in a ratio of 0.01 to 0.1:99.99 to 99.9, is more preferably a mixture of lyophilized lactic acid bacteria and a medium powder in a ratio of 0.05 to 0.1:99.95 to 99.9, is even more preferably a mixture of lyophilized lactic acid bacteria and a medium powder in a ratio of 0.1:99.9 and preferably further includes a mold growth inhibitor. The mold growth inhibitor according to the present invention is preferably selected from the group consisting of polyene antifungals, nystatin, amphotericin B and pimaricin.

In the present invention, *lactobacillus acidophilus* as lactic acid bacteria are cultured in several media for 0 to 21 days. As a result, lactic acid or the like is produced when *lactobacillus acidophilus* grows, thus causing a decrease in pH. It can be seen that the decreased pH is maintained for 3 weeks. The lactic acid bacteria are cultured with a pH marker such as a pH indicator, metallic soap particles and pH sensitive polymer particles. As a result, lactic acid bacteria grew, thus causing a pH decrease and the medium changes color, indicating an acid. At this time, metallic soap particles and pH sensitive polymer particles maintain the acidic color although the medium is adjusted to neutrality. The bacteria should survive even at a freezing temperature (e.g., −20° C.) and grow upon temperature elevation so as to effectively use the freeze-stored label of the present invention.

In order for the label to effectively conduct its functions when the temperature drops to a freezing point or less during use of the label of the present invention in a storage area, bacteria should survive even at the freezing point or less. First of all, lactic acid bacteria should at least survive although they do not grow during storage at a low temperature for a long time. Although lactic acid bacteria are cultured after freezing-storage, it can be cultured, like bacteria cultured without freezing-storage or bacteria cultured after cold-storage and causes a pH decrease of the culture medium immediately after it is cultured. In addition, the lactic acid bacteria according to the present invention should be lyophilized and then cultured at different seeding concentrations, and the lyophilized lactic acid bacteria should be used in an amount of 0.1% (W/V) or less so as to not have an effect such as turbidity by other matter on determination of color of the medium and CFU should be 10,000 CFU/mL or more so as to complete growth of bacteria within 1 to 2 days.

According to the present invention, it is possible to determine decay of a stored substance by exposing a label including lyophilized lactic acid bacteria and a pH indicator to different temperatures and comparing the color of the pH indicator depending on the culture condition of microorganisms. The label of the present invention is useful for determining decay feasibility of a stored substance depending on cumulative storage temperature change.

Any microorganism can be used as the lactic acid bacteria according to the present invention so long as it has a similar growth pattern to *E. coli* O-157 or *salmonella*, which are representative putrefying food poisoning bacteria, produces an organic acid during growth, thus causing a decrease in pH, and is harmless to humans and the environments, and preferably includes lactic acid bacteria, yeast, mold or the like, most preferably is *lactobacillus acidophilus*.

The medium according to the present invention has a composition, pH of which is decreased by an organic acid that is produced when lactic acid bacteria grow and is preferably selected from MRS, a medium diluted with MRS (25%), a minimal medium and a minimal medium containing 100 g/L of glucose lactic acid bacteria and is more preferably a medium diluted with MRS (25%).

In the present invention, pH of the medium where lactic acid bacteria do not grow is controlled to neutrality and, when an amino acid ingredient is rich in the medium, it is decomposed by lactic acid bacteria to produce ammonia which causes a pH increase. For this reason, the amount of amino acid is reduced. As lactic acid bacteria grow more, the amount of produced organic acid increases. The organic acid decreases a pH of the medium, leading to acidity. If an indicator which changes color when pH decreases is added to a medium, lactic acid bacteria that have undergone the same temperature change as the stored substance grow and, at the same time, causing a color change. The lactic acid bacteria can grow when putrefying bacteria are present in the stored substance.

The lactic acid bacteria powder mixture according to the present invention is a mixture of lyophilized lactic acid bacteria and a medium powder in a ratio of 0.01 to 0.1:99.9 to 99.99, preferably a ratio of 0.05 to 0.1:99.9 to 99.95, most preferably a ratio of 0.1:99.9.

In order to remove the necessity of maintaining asepsis in the production of the label of the present invention, lactic acid bacteria are produced by previously mixing lactic acid bacteria in the form of a lyophilized powder with a medium powder and isolating the same from water. In this case, culture of other bacteria can be inhibited, but asepsis is not created. For this reason, the mold is incorporated and grows during culture of lactic acid bacteria, decomposes an organic acid, increases pH and changes color. In order to solve these phenomena, the powder mixture of the present invention may further include a mold growth inhibitor and the mold growth inhibitor may include polyene antifungals, nystatin, amphotericin B, pimaricin or the like.

Any indicator clearly showing color change under neutral and acidic conditions can be used as the pH indicator according to the present invention and is preferably methyl red, methyl blue, bromocresol green-methyl red, bromocresol green, bromophenol blue or the like.

According to the present invention, in a case in which pH of the culture medium decreased by an organic acid produced during growth of lactic acid bacteria is increased again due to growth of other contaminant bacteria or the like, neutral pH may be obtained. For this reason, color change should be prevented despite of pH increase. Once color is changed due to low pH, a method for maintaining the color is needed.

The pH indicator liquid 22 according to the present invention is preferably a pH indicator liquid containing distilled water. The pH indicator used as a pH marker in the present invention may be metallic soap particles and pH sensitive polymer particles as well as a general pH indicator.

The general pH indicator according to the present invention preferably clearly exhibits color change and is preferably a mixture of methyl red and methyl blue. Any pH indicator can be used in the present invention so long as it clearly shows color change under neutral and acidic conditions and preferably includes methyl red, methyl blue, bromocresol green-methyl red, bromocresol green, bromophenol blue or the like. The pH indicator liquid 22 according to the present invention is preferably a pH indicator liquid containing distilled water.

The pH indicator according to the present invention is produced by dissolving 0.1 g of methyl red, 0.1 g of methylene blue in 190 mL of ethanol and filling the balance of water to obtain the total weight of 200 mL. Any indicator that changes color in the range from neutrality to acidity can be used.

The pH indicator according to the present invention preferably includes metallic soap particles or pH sensitive polymer particles and the metallic soap particles are preferably metallic soap grains produced by saponifying a dye and oleic acid with divalent ions.

The metallic soap particles of the present invention are obtained as metal soap particles by saponifying a dye and oleic acid with divalent ions such as calcium ions. When pH is decreased due to organic acid, the metal soap is decomposed again, the dye contained therein is dispersed and the label entirely shows the color of the dye. In this reaction, because the dye of the ingredient in the label does not voluntarily become metal soap particles again, although pH changes to a neutral level over time, the color of the label can be maintained.

The metal soap of the present invention is produced in the form of metal soap particles by saponifying a dye and oleic acid with calcium divalent ions. More specifically, 10 mg of D&C Red No. 6 barium-lake, 15 g of oleic acid, 2.204 g of $Ca(OH)_2$, 5.67 g of $H_2O$ and 0.0375 g of lipase at 60° C. are reacted at 480 rpm for 2.5 hours and then finely ground before use.

The pH indicator according to the present invention is preferably a pH-sensitive polymer selected from the group consisting of chitosan, polylysine, polyethylenimine (PEI), diethylaminoethyl-dextran (DEAE-dextran) and poly(amidoamine) (PAMAM) dendrimers.

The pH sensitive polymer particles according to the present invention are produced such that an expanding basic polymer as the polymer traps the dye at a low pH, when pH is decreased due to an organic acid, the dye trapped in polymer particles is released to the medium, thus showing the color of the dye and, although a neutral pH is obtained again, the dye is not incorporated in the contracted polymer particles again, thus maintaining the color of the dye. The basic polymer according to the present invention may be chitosan, polylysine, polyethylenimine (PEI), diethylaminoethyl-dextran (DEAE-dextran), poly(amidoamine) (PAMAM) dendrimers or the like. The dye according to the present invention may be D&C Red No. 6 Barium-lake, a red organic dye or inorganic dye, or the like.

The pH-sensitive polymer according to the present invention may be selected from a variety of basic polymers and may be any basic polymer expanding at a low pH.

Strength can be improved by dissolving 0.5 g of chitosan in 50 mL of an 0.1% (V/V) acetic acid and adding 3 to 80% (wt %) of EDTA with respect to the weight of chitosan. 1 to 5 mg of a dye (D&C Red No. 6 Barium-lake, Warner-Jenkinson, USA) is added to the resulting mixture and pH neutralization is conducted with 5M NaOH. EDAC [1-Ethyl-3-(3-dimethylaminopropyl) carbodiimide hydrochloride. Sigma, USA] is added to the resulting mixture to a concentration of 10 to 100 mM. The reaction solution is stirred at room temperature for 4 hours, washed twice with distilled water and twice with 0.5 M NaCl and twice with 0.025M NaOH and then once with distilled water and then refrigerated.

In order for the label of the present invention to effectively conduct its functions when the temperature drops to a freezing point or less during use in a storage area, the putrefying bacteria of the stored substance should survive even at a freezing point or less. The determination of whether a stored substance has decayed can be carried out by exposing a label including lyophilized lactic acid bacteria and a pH indicator to different temperatures and comparing the color of the pH indicator. The label of the present invention is useful for determining decay feasibility of a stored substance depending on cumulative storage temperature change.

In the present invention, in a case in which pH increases again, pH may fall into a neutral range. For this reason, although pH increases, color should not change. Once color is changed due to low pH, a method for maintaining the color is needed. The metallic soap particles and pH sensitive polymer particles according to the present invention may be more useful.

The label of the present invention can be produced in a form of a label that can be attached to the outside of the food storage container. The label of the present invention is produced as a label directly attached to an exterior container of the stored substance decayed due to temperature and is thus used to measure a true temperature change of the stored substance, rather than the temperature of the storage area during storage and transportation.

In order to check a pH change resulting from lactic acid bacteria and color change of a pH marker, the pH change resulting from lactic acid bacteria and the color change of the pH marker are checked at 30° C. using lactic acid bacteria and a pH indicator, metallic soap particles and pH sensitive polymer particles at concentrations of 0.0001%, 1% and 1%, respectively. Finally, pH is adjusted to a neutral level and color change is checked. The pH indicator, which is an indicator showing green at first, changes to purple and red and then maintains the color, whereas the metallic soap particles and pH sensitive polymer particles maintain the original color, red, although they are kept at a neutral level.

The label of the present invention is attached to an exterior container of the stored substance, when the stored substance is decayed at an exterior temperature increasing from −10 to 40° C. as storage time passes, the separation membrane 50 is selectively dissolved at the exterior temperature of −10 to 40° C. and the color of the pH indicator is changed and the stored substance is determined to be decayed when the changed color of the label indicates acidity.

The label produced to check the color change depending on the storage temperature change according to the present invention is exposed to different temperatures of −10° C., 0° C., 4° C., 5° C., 10° C., 15° C., 20° C., 25° C., 30° C., 35° C., 37° C. and 40° C. for a predetermined time and color change is observed in each range. When the indicator changes color, decay feasibility can be determined based on the color change.

The surface separation membrane 40 of the label according to the present invention is a film produced using a material such as polyethylene (PE), polypropylene (PP), polystyrene (PS) or polyethylene terephthalate (PET) to protect an inner material from the pressure applied for attachment. A lower attachment surface is preferably non-transparent white to prevent confusion with the color of the stored substance.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An exterior temperature-detectable selectively dissoluble lactic acid bacteria separation membrane functional label for checking freshness of a stored substance comprising:
   a pH indicator layer attached to the surface of an upper part of a label;
   a lactic acid bacteria layer attached to the surface of the upper part of the label and separated from the pH indicator layer; and
   a separation membrane for separating the pH indicator layer from the lactic acid bacteria layer, wherein the separation membrane comprises
   glucose, maltose, fructose, or sucrose;
   starch;
   a phase-transfer coating agent; and
   a phase-transfer inducing catalyst,
   wherein the pH indicator layer comprises any one indicator selected from a pH indicator powder and a pH indicator liquid, the lactic acid bacteria layer comprises a lactic acid bacteria liquid and the separation membrane comprises a separation membrane for detecting an exterior temperature selectively dissolved at an exterior temperature of −10 to 40 degrees Celsius.

2. The exterior temperature-detectable selectively dissoluble lactic acid bacteria separation membrane functional label according to claim 1,
   wherein the phase-transfer coating agent comprises a linseed oil free of odor and cyanide (—CN) toxicity which is prepared by heating linseed at 100° C. for 20 minutes, removing moisture from the linseed, rapidly cooling the residue, obtaining an linseed oil from the rapidly cooled linseed in an oil extruder at a temperature of 100° C., filtering the linseed oil through a 200 mesh sieve to obtain the filtered linseed oil, allowing the filtered linseed oil to be precipitated for 20 days and collecting the supernatant to obtain a purified linseed oil.

3. An exterior temperature-detectable selectively dissoluble lactic acid bacteria separation membrane functional label for checking freshness of a stored substance comprising:
   a pH indicator layer attached to the surface of an upper part of a label;
   a lactic acid bacteria layer attached to the surface of the upper part of the label and separated from the pH indicator layer; and
   a separation membrane for separating the pH indicator layer from the lactic acid bacteria layer,
   wherein the pH indicator layer comprises a pH indicator liquid, the lactic acid bacteria layer comprises a lactic acid bacteria powder and the separation membrane comprises a separation membrane for detecting an exterior temperature which is selectively dissolved at an exterior temperature of −10 to 40 degrees Celsius.

4. The exterior temperature-detectable selectively dissoluble lactic acid bacteria separation membrane functional label according to claim 1, wherein the label comprises the pH indicator layer and the lactic acid bacteria layer which are separated from each other in a container.

5. The exterior temperature-detectable selectively dissoluble lactic acid bacteria separation membrane functional label according to claim 1, wherein the label comprises a plurality of containers attached to the surface of the upper part of the label and the separation membranes of respective containers are selectively dissolved at different temperatures.

6. The exterior temperature-detectable selectively dissoluble lactic acid bacteria separation membrane functional label according to claim 1, wherein the separation membrane comprises glucose.

7. The exterior temperature-detectable selectively dissoluble lactic acid bacteria separation membrane functional label according to claim 1, wherein the separation membrane comprises maltose.

8. The exterior temperature-detectable selectively dissoluble lactic acid bacteria separation membrane functional label according to claim 1, wherein the separation membrane comprises fructose.

9. The exterior temperature-detectable selectively dissoluble lactic acid bacteria separation membrane functional label according to claim 1, wherein the separation membrane comprises sucrose.

* * * * *